US009044248B2

(12) United States Patent
Benscoter et al.

(10) Patent No.: US 9,044,248 B2
(45) Date of Patent: *Jun. 2, 2015

(54) CATHETER DEFLECTION ANCHOR

(71) Applicant: Medtronic Ablation Frontiers LLC, Minneapolis, MN (US)

(72) Inventors: Mark Allen Benscoter, Dellwood, MN (US); Stuart Brahm Kozlick, Cote-St-Luc (CA); Jeremy David Dando, Plymouth, MN (US)

(73) Assignee: Medtronic Ablation Frontiers LLC, Minneapolis, MN (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/204,655

(22) Filed: Mar. 11, 2014

(65) Prior Publication Data
US 2014/0194814 A1    Jul. 10, 2014

Related U.S. Application Data

(63) Continuation of application No. 13/450,855, filed on Apr. 19, 2012, now Pat. No. 8,702,647.

(51) Int. Cl.
*A61M 25/01*   (2006.01)
*A61B 18/14*   (2006.01)
*A61B 1/005*   (2006.01)
*A61B 1/012*   (2006.01)

(52) U.S. Cl.
CPC .......... *A61B 18/1492* (2013.01); *A61B 1/0057* (2013.01); *A61M 25/0147* (2013.01); *A61B 1/0125* (2013.01); *Y10T 156/1031* (2013.01); *A61M 2025/015* (2013.01)

(58) Field of Classification Search
USPC ................................ 600/146; 604/528, 95.04
See application file for complete search history.

(56) References Cited

U.S. PATENT DOCUMENTS

| | | | | |
|---|---|---|---|---|
| 5,364,352 A | * | 11/1994 | Cimino et al. | 604/95.04 |
| 5,960,145 A | | 9/1999 | Sanchez | |
| 6,083,222 A | | 7/2000 | Klein et al. | |
| 6,146,355 A | * | 11/2000 | Biggs | 604/95.01 |
| 6,616,628 B2 | | 9/2003 | Hayzelden | |
| 6,991,616 B2 | * | 1/2006 | Bencini et al. | 604/95.01 |
| 7,089,063 B2 | | 8/2006 | Lesh et al. | |
| 7,955,298 B2 | | 6/2011 | Carroll et al. | |
| 7,985,215 B2 | | 7/2011 | Guo et al. | |
| 2002/0096177 A1 | * | 7/2002 | Toti et al. | 128/207.15 |
| 2003/0181855 A1 | * | 9/2003 | Simpson et al. | 604/95.04 |
| 2004/0037921 A1 | * | 2/2004 | Hokkirigawa et al. | 426/59 |
| 2004/0087921 A1 | * | 5/2004 | Guldfeldt et al. | 604/349 |
| 2008/0091169 A1 | | 4/2008 | Heideman et al. | |
| 2008/0131765 A1 | | 6/2008 | Imanaga et al. | |

(Continued)

FOREIGN PATENT DOCUMENTS

DE   102010019213 A1   11/2011
JP       2004283461 A   10/2004

*Primary Examiner* — Nicholas Lucchesi
*Assistant Examiner* — Gerald Landry, II
(74) *Attorney, Agent, or Firm* — Christopher & Weisberg, P.A.

(57) ABSTRACT

A system and method for anchoring a round catheter pull wire within the distal end of a catheter. A steering deflection mechanism includes a pull ring having a plurality of apertures and one or more receiving slots. The method includes affixing one or more round pull wires to the one or more receiving slots of the pull ring. The shape of the round wire and manner of affixing the wire to the pull ring provide a steering assembly that can withstand greater pull forces while maintaining design integrity.

15 Claims, 9 Drawing Sheets

(56) References Cited

U.S. PATENT DOCUMENTS

| | | |
|---|---|---|
| 2008/0161798 A1 | 7/2008 | Podmore et al. |
| 2008/0234660 A2 * | 9/2008 | Cumming et al. .......... 604/527 |
| 2009/0163915 A1 | 6/2009 | Potter |
| 2009/0163917 A1 | 6/2009 | Potter |
| 2010/0152590 A1 | 6/2010 | Moore et al. |
| 2010/0168666 A1 | 7/2010 | Tegg |
| 2012/0101442 A1 | 4/2012 | Legaspi et al. |
| 2012/0108938 A1 | 5/2012 | Kauphusman et al. |

* cited by examiner

CATHETER DEFLECTION ANCHOR

CROSS-REFERENCE TO RELATED APPLICATION

This application is a continuation of patent application Ser. No. 13/450855, filed Apr. 19, 2012, entitled CATHETER DEFLECTION ANCHOR, the entirety of which is incorporated herein by reference

STATEMENT REGARDING FEDERALLY SPONSORED RESEARCH OR DEVELOPMENT n/a

FIELD OF THE INVENTION

The present invention relates to a system and method for anchoring a catheter pull wire within the distal end of a catheter.

BACKGROUND OF THE INVENTION

Catheters are commonly used to perform medical procedures within very small spaces in a patient's body, and most procedures mandate precise catheter navigation. A catheter used to perform many ablation and mapping procedures generally includes a handle and a flexible elongate body (or shaft) having a distal end. Steering the distal end of a catheter can be difficult, especially as the elongate body passes through a tortuous vascular path.

Catheter tip steering is often accomplished with the use of one or more pull wires attached to a pull ring within the distal end of the catheter shaft at one end, and coupled to a steering control mechanism housed within the handle at the other end. Manipulation of the steering control mechanism will deflect the catheter tip through pulling or releasing pull force pressure on the one or more pull wires. The pull force exerted on a pull wire within a standard-sized catheter is often quite large, for example, in excess of ten pounds, and the pull force required is increased for thicker or longer catheters. Therefore, the point of connection between a pull wire and the pull ring must be able to withstand this force in order to preserve the integrity of the steering system.

Currently, the most frequently used type of joining method between a pull wire and pull ring is welding the distal end of a flat pull wire to an outer surface of a pull ring. However, this joining method is very susceptible to stress fractures and peeling as a pull force is exerted repeatedly over time (referred to herein as "destructive pull force" to distinguish from the pull force necessary to steer the catheter tip). Sometimes a round pull wire may be used that has a flattened distal end for attachment to the pull ring, but this does not provide a significant benefit over using a flat pull wire. The point in the pull wire at which the flat distal end transitions into the rounded wire body becomes another stress point when the catheter tip is repeatedly deflected. As a result, the pull wire may become detached from the pull ring, or may break at the stress point. Further, it is not uncommon for pull rings to become detached from the inside of the catheter shaft and creep away from the distal end of the catheter as a result of repeated deflections and manipulations.

A system and method of anchoring a pull wire to a pull ring in a catheter deflection mechanism is provided herein. Further provided is a system and method to enhance the strength of the join between a pull wire and pull ring so that the mechanism may reach higher levels of pull force while maintaining design integrity. For example, the system and method include an increased amount of weld sites for attaching a pull wire to a pull ring.

SUMMARY OF THE INVENTION

The present invention advantageously provides a method and system for anchoring a round catheter pull wire within the distal end of a catheter. The system includes a catheter steering device including an annular band having a plurality of apertures and a receiving slot. The receiving slot is sized to longitudinally receive a wire having a circular cross section, and the wire is coupled to the band in more than two locations. For example, the wire may be welded to the band in four locations. The band has a thickness, a first edge, a second edge, and a height between the first and second edges that is greater than the thickness. Further, the band may have a first, second, and third aperture. The first aperture may be located approximately 180° from a center line of the receiving slot, and a center point of the second and third aperture may each be located approximately 120° from either side of the center point of the first aperture. The receiving slot may continue from the first edge to the second edge of the band, or the receiving slot may continue from the first edge to a point between the first and second edges.

Alternatively, the band may include a first, second, third, and fourth aperture, and a first and second receiving slot. A center point of the first and second aperture may each be located between approximately 40° and approximately 50° from either side of a center line of the first receiving slot, and a center point of the third and fourth aperture may each be located between approximately 40° and approximately 50° from either side of a center line of the second receiving slot, and the center points of the first and second apertures may be located approximately 180° from each other. The receiving slots may have a keyhole shape, and the pull wire may have a substantially spherical knob at its distal tip.

The assembly may further include a fusible band in contact with the inner surface of the annular band, and the fusible band may be composed of a thermoplastic. The assembly may further include a marker band located a predetermined distance form the first edge of the annular band.

The method includes forming an annular inner band composed of thermoplastic into a cylinder shape, the inner band having a first height, forming an annular anchor band about the inner band, the anchor having a second height that is less than the first height, the anchor band including therein a plurality of apertures and a receiving slot, inserting the distal end of a pull wire having a circular cross section into the receiving slot of the anchor band and welding the pull wire to the anchor band, and heating the inner band to at least the minimum melt temperature of the thermoplastic. The method may further include forming an annular marker band composed of a radiopaque material about the inner band a predetermined distance from the anchor band, the marker band having a third height that is less than the first height.

BRIEF DESCRIPTION OF THE DRAWINGS

A more complete understanding of the present invention, and the attendant advantages and features thereof, will be more readily understood by reference to the following detailed description when considered in conjunction with the accompanying drawings wherein.

DETAILED DESCRIPTION OF THE INVENTION

As used herein, the term "steering deflection anchor," "deflection anchor," or "pull wire anchor" refers to a pull ring. Further, the term "steering deflection mechanism" or "anchor mechanism" includes the pull ring (or deflection anchor) and pull wire, and may optionally include an inner layer of thermoplastic and a marker band.

As used herein, the term "round pull wire" refers to a longitudinally extended catheter pull wire that is round or circular in cross section.

Figure 1:
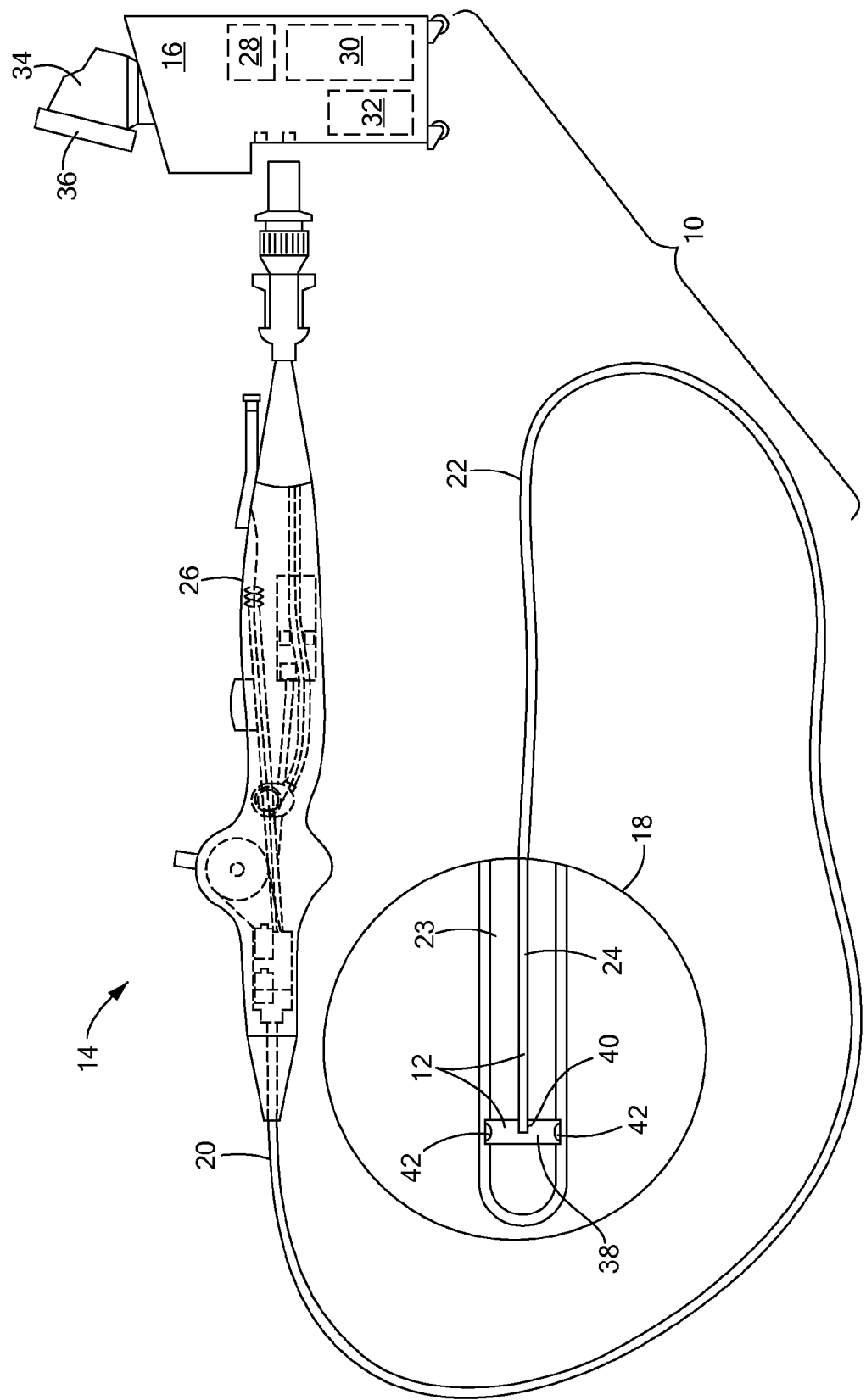
FIG. 1 shows a system including the steering deflection mechanism described herein.

Referring now to FIG. 1, a system 10 including a steering deflection mechanism 12 is shown. The steering deflection mechanism 12 may generally include a pull wire anchor 38 (or pull ring) and one or more pull wire. The system 10 may generally include a medical device 14 (for example, an ablation or mapping catheter) and a console 16. The medical device 14 may include a distal end 18, a proximal end 20, and a flexible elongate shaft 22 having one or more lumens therein 23. The distal end 18 of the flexible elongate shaft 22 may be capable of in-plane and/or out-of-plane deflection and is steerable by one or more pull wires 24. The proximal end 20 of the medical device 14 may be affixed to a handle 26 having various inlets, outlets, steering control mechanisms (for example, knobs, toggles, etc.). Further, the one or more pull wires 24 may be either coupled to or routed through the handle 26. The medical device 14 may be in fluid and/or electrical communication with a console 16 that may include an energy generator 28 (for example, a radio frequency generator), a refrigerant reservoir 30, a power source 32, a computer 34, a display 36, and/or various user control devices (for example, buttons, knobs, valves, keyboard, touch screen, foot pedals, etc.). The medical device 14 and console 16 may be adapted for treatment using any energy modality (for example, cryoablation, radio frequency ablation, laser ablation, and/or microwave ablation) and/or medical procedure that is facilitated by using a steerable catheter (for example, cardiac mapping).

The pull wire anchor 38 (also referred to as "pull ring") of the steering deflection mechanism 12 is affixed to the inside of the distal end 18 of the device 14 shaft 22 and the one or more pull wires 24 are coupled to the pull ring 38. When a user manipulates the pull wires 24, the distal end 18 of the medical device 14 is deflected (that is, steered) in the direction of the force being exerted on the pull ring 38 by the one or more pull wires 24. As is shown in greater detail in FIGS. 2-10, the pull ring 38 may generally include one or more receiving slots 40, each of which receiving a pull wire 24, and a plurality of apertures 42.

Figure 2:
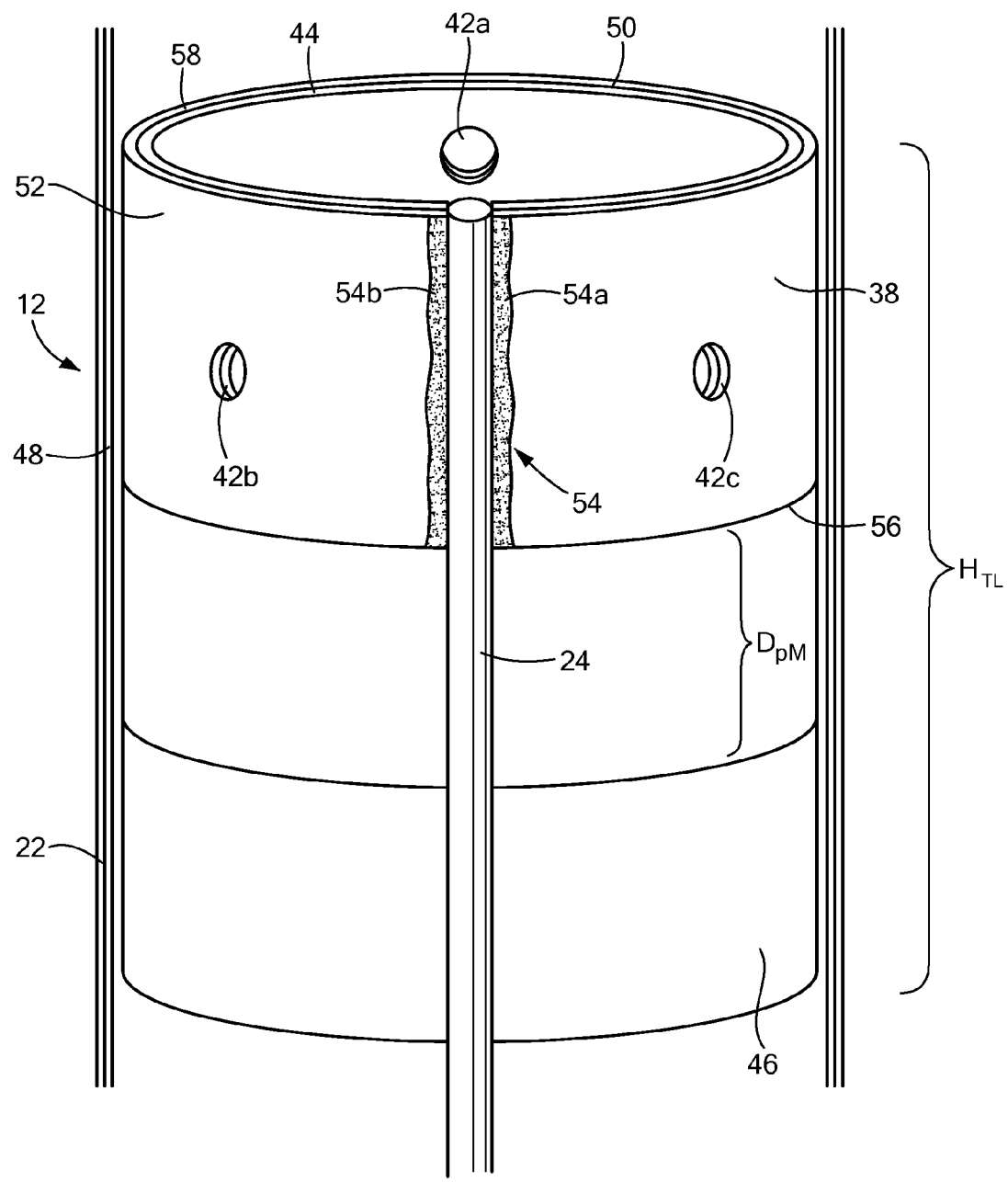
FIG. 2 shows a perspective view of a steering deflection mechanism within a medical device shaft.
Figure 3:
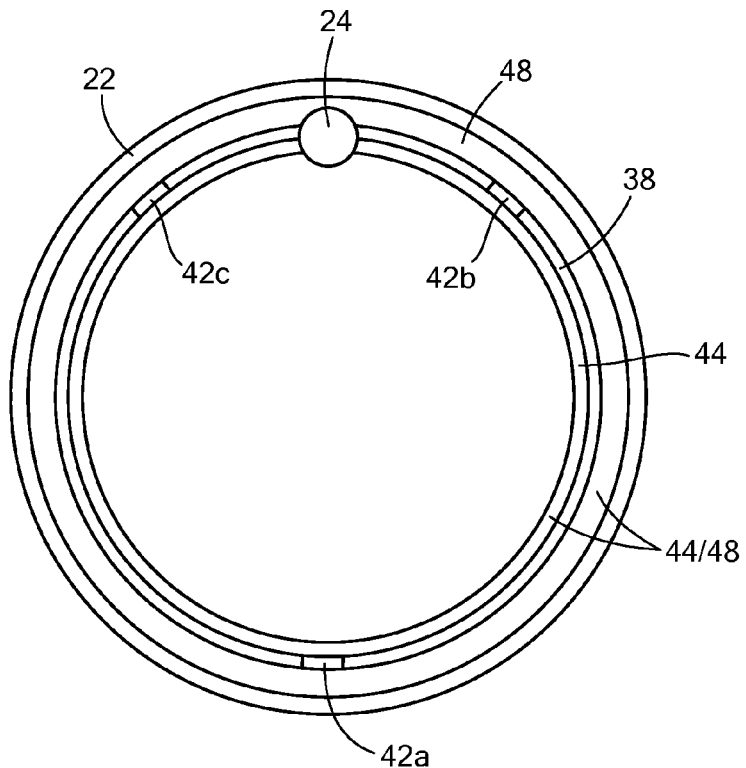
FIG. 3 shows a cross-sectional view of a medical device shaft including the steering deflection mechanism of FIG. 2.

Referring now to FIG. 2, a steering deflection mechanism 12 within a medical device 14 shaft 22 is shown. The medical device 14 may be a catheter, as shown in FIG. 2. The steering deflection mechanism 12 (or anchor mechanism) as shown in FIG. 2 generally includes a pull ring 38 and a pull wire 24 having a circular or round cross section (also referred to as a "round pull wire"). As described in FIGS. 5-7, the pull ring 38 has a height H. The steering deflection mechanism 12 may further include an inner ring layer 44 of thermoplastic elastomer (for example, Pebax®) and a marker band 46, as shown in FIGS. 2 and 3. The steering deflection mechanism 12 is located in the distal end 18 of a catheter shaft 22, and the shaft 22 may include a lining 48 composed of the same thermoplastic as the inner ring layer 44. Thermoplastic in general, such as when the inner ring layer 44 and shaft lining 48 melt together, is referred to as "thermoplastic 44/48." The thermoplastic inner ring layer 44 is in contact with the inner surface 50 of the pull ring 38 and may be approximately 0.05 mm to approximately 0.5 mm thick. Further, the thermoplastic inner ring layer 44 may have a height $H_{TL}$ that is greater than the height H of the pull ring 38. If a marker band 46 is included, the height $H_{TL}$ of the thermoplastic inner ring layer 44 may be large enough to both line the inner surface 50 of the pull ring 38 and extend a substantial portion of a predetermined distance $D_{PM}$ between the pull ring 38 and marker band 46. The distance $D_{PM}$ between the pull ring 38 and marker band 46 may depend on such considerations as the procedure for which the catheter 14 will be used and the type of catheter navigation system used.

The steering deflection mechanism 12 may be coupled to the catheter shaft 22 by heating the shaft 22 to a melting temperature of the thermoplastic 44/48 used in the steering deflection mechanism 12 and the shaft inner lining 48. Specifically, as the thermoplastic 44/48 is heated and melts, the thermoplastic inner ring layer 44 of the steering deflection mechanism 12 will meld or blend with the thermoplastic inner lining 48 of the catheter shaft 22, thereby affixing the steering deflection mechanism 12 to the distal end 18 of the catheter 14. Further, melted thermoplastic 44/48 will also flow through the apertures 42 in the pull ring 38 to give added strength to the anchor mechanism 12/shaft 22 point of connection when the thermoplastic 44/48 hardens. Still further, the marker band 46 will also become affixed to the distal end 18 of the catheter shaft 22 by the thermoplastic 44/48. The round pull wire 24 may pass along the inside of the marker band 46 (as shown in FIG. 2) or on the outside of the marker band 46 (not shown).

Referring now to FIG. 3, a cross-sectional view of a medical device 14 (for example, catheter) shaft 22 including the steering deflection mechanism 12 of FIG. 2 is shown. The cross section shows a typical distribution of thermoplastic 44/48 between the inner lining 48 of the catheter shaft 22 and the steering deflection mechanism 12. As shown and described in FIG. 2, melted thermoplastic 44/48 of the catheter shaft inner lining 48 and the inner ring layer 44 of the steering deflection mechanism 12 will meld or blend as the melting temperature of the thermoplastic 44/48 is reached. As the shaft 22 is allowed to cool, the thermoplastic 44/48 will harden and thereby strengthen the point of connection between the distal end 18 of the catheter shaft 22 and the steering deflection mechanism 12. Although not shown in FIG. 3, the catheter shaft 22 may include additional layers or elements.

Figure 4:
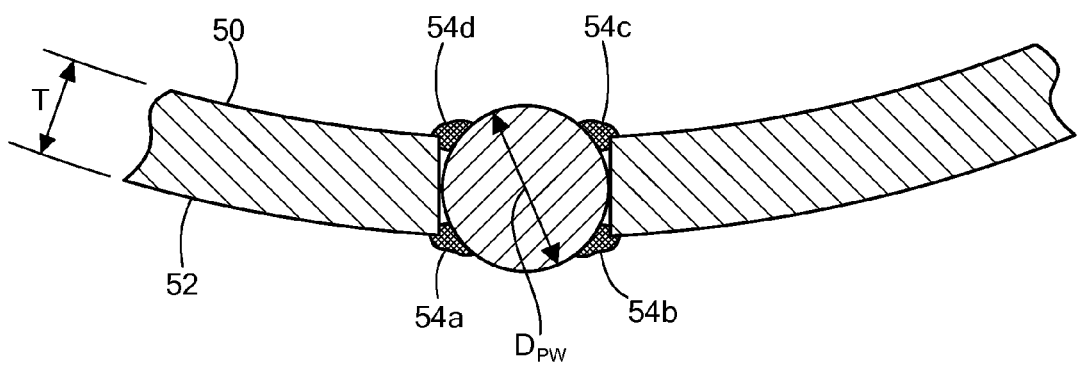
FIG. 4 shows a top detail view of a round pull wire received within and welded to a pull wire anchor.

Referring now to FIG. 4, a top detail view of a round pull wire 24 received within and welded to a pull wire anchor 38 is shown. For simplicity, a top view of a break-type receiving slot 40 and straight round pull wire 24 (such as those shown in FIGS. 6 and 9) is shown is shown in FIG. 4. The pull ring 38 has an inner surface 50 and an outer surface 52. The inner 50 and outer 52 surfaces may have the same or different textures, such as smooth, ridged, knurled, scored, or the like. From the top view, four weld sites 54a, 54b, 54c, 54d between a round pull wire 24 and pull ring 38 are seen. Because the round pull wire 24 has a diameter $D_{PW}$ that is greater than the thickness T of the pull ring 38, the round pull wire 24 may be welded to the pull ring 38 in four discrete locations: two weld lines 54a, 54b on the outer surface 52 of the pull ring 38 along the receiving slot 40, and two weld lines 54c, 54d on the inner surface 50 of the pull ring 38 along the receiving slot 40. Thus, increased number of weld sites doubles the connection strength between the pull wire 24 and pull ring 38, which is a significant advantage over existing systems that use a flat wire within a receiving slot 40. Further, use of a round wire 24 (instead of a flat wire or found wire with a flat distal end) allows for an even distribution of stress caused by destructive pull forces, rather than centering stress in the transition location of a flattened round wire or along one plane in a flat wire. In other words, the present embodiments enable the steering mechanism to reach higher levels of force while maintaining design integrity.

Figure 5:
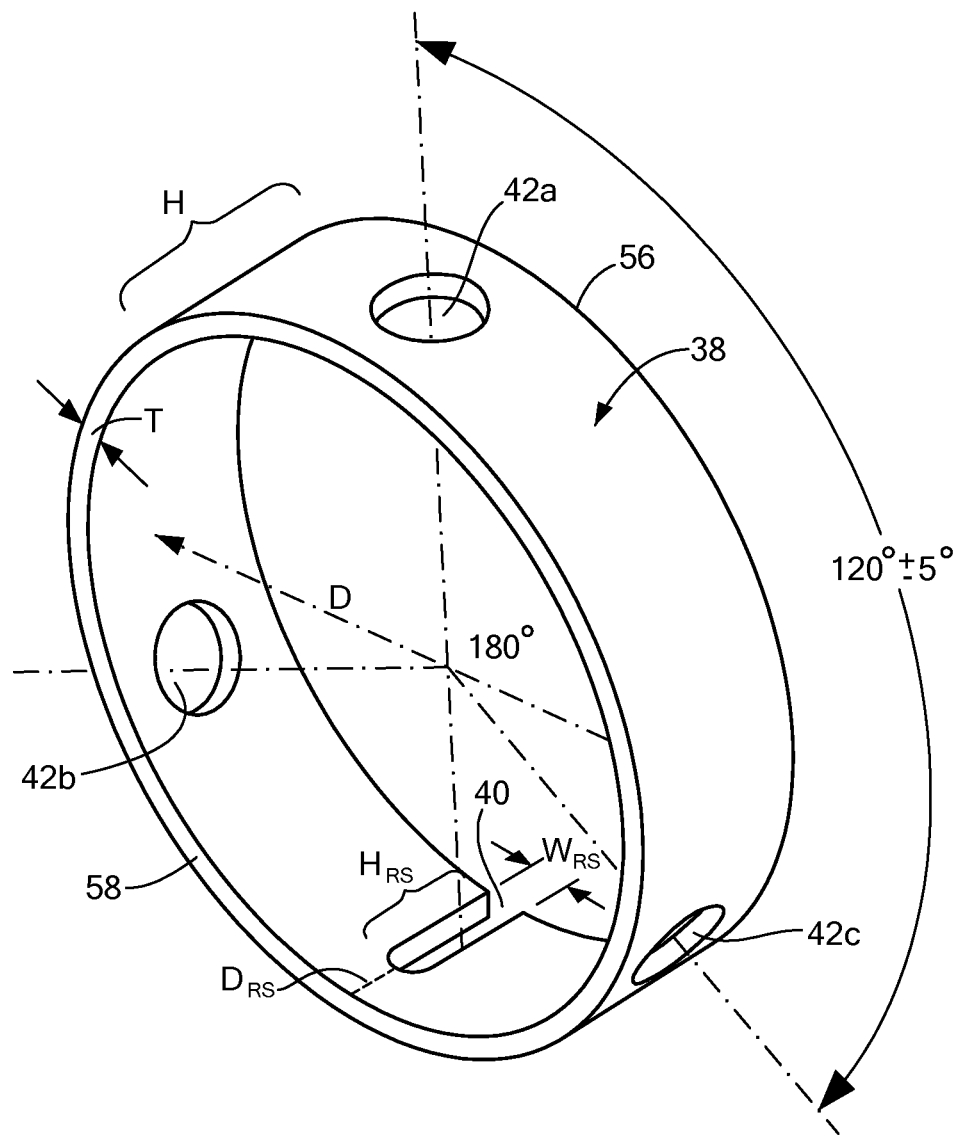
FIG. 5 shows a perspective view of a first embodiment of a pull wire anchor.

Referring now to FIG. 5, a first embodiment of a pull wire anchor 38 (pull ring) is shown. The pull ring 38 may generally include a receiving slot 40 and a plurality of apertures 42. The pull ring 38 is an annular band having a height H, a thickness T, and a diameter D. The height H is greater than the thickness T. As a non-limiting example, the height H may be approximately 1.50 mm, the thickness T may be approximately 0.15 mm, and the diameter D may be approximately 2.00 mm. However, the pull ring 38 may have any dimensions that are appropriate for the pull wire 24 and catheter 14 assembly used. The pull ring 38 also has a first edge 56 and a second edge 58, used herein as reference points for describing the locations of other features of the system and method. The pull ring 38 may be continuous along the second edge 58, but the continuity of the first edge 56 may be disrupted by the receiving slot 40. Further, the pull ring 38 may be composed of any suitable material, such as stainless steel, titanium, Nitinol, or alloy such as 304V spring temper.

Figure 7:
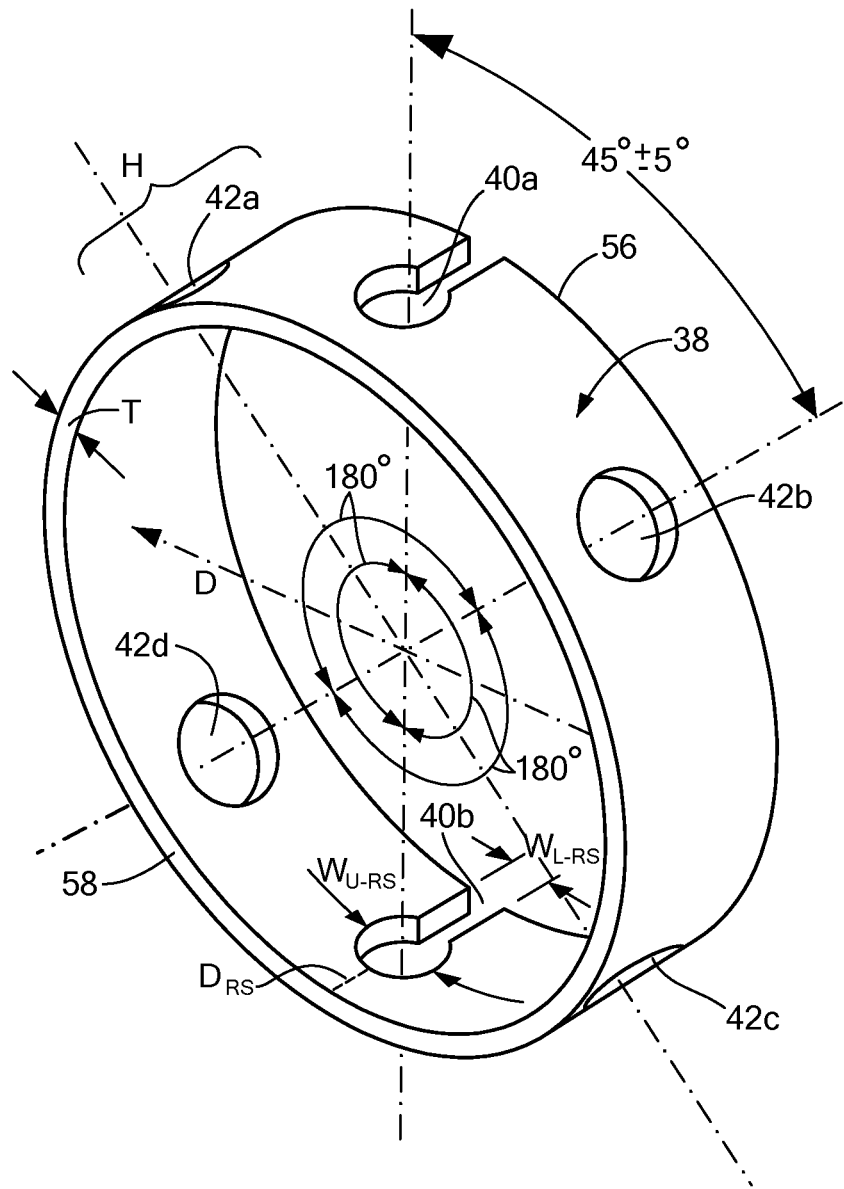
FIG. 7 shows a perspective view of a third embodiment of a pull wire anchor.
Figure 8:
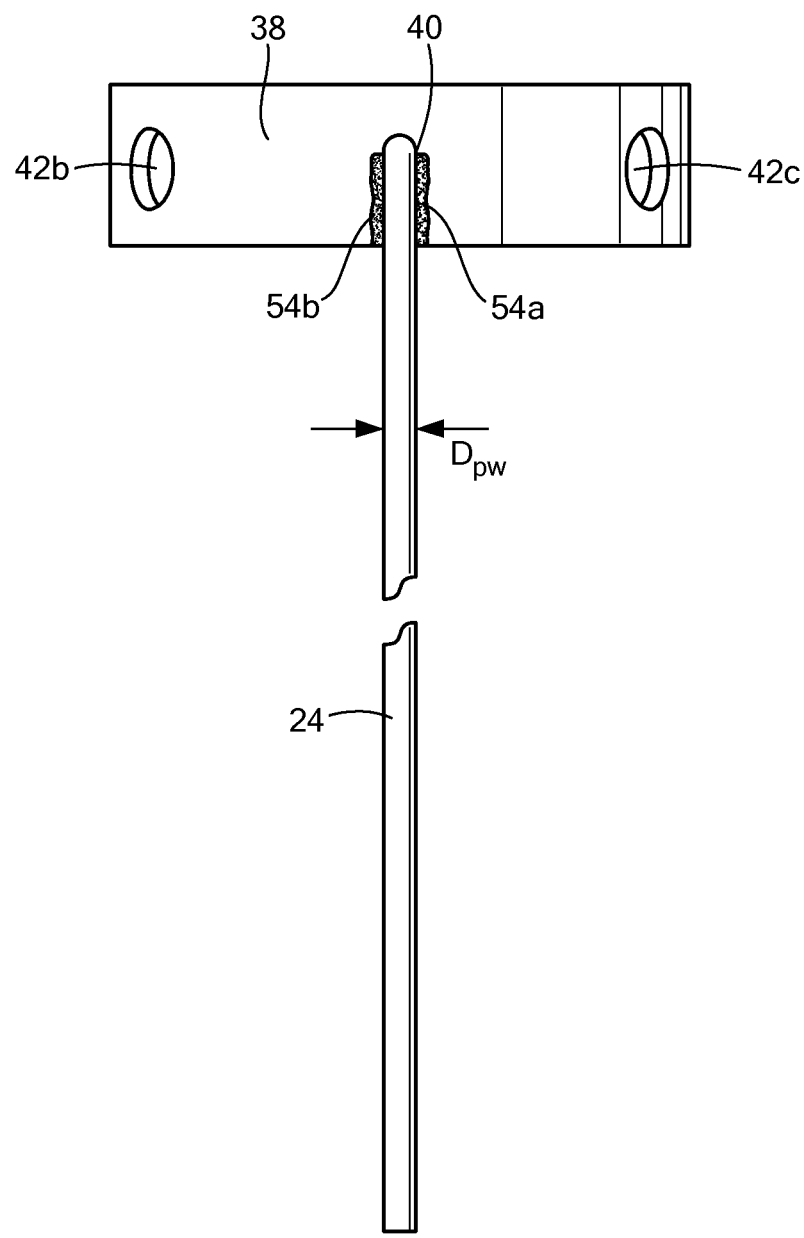
FIG. 8 shows a side view of a straight round pull wire received within and welded to the first embodiment of a pull wire anchor.
Figure 9:
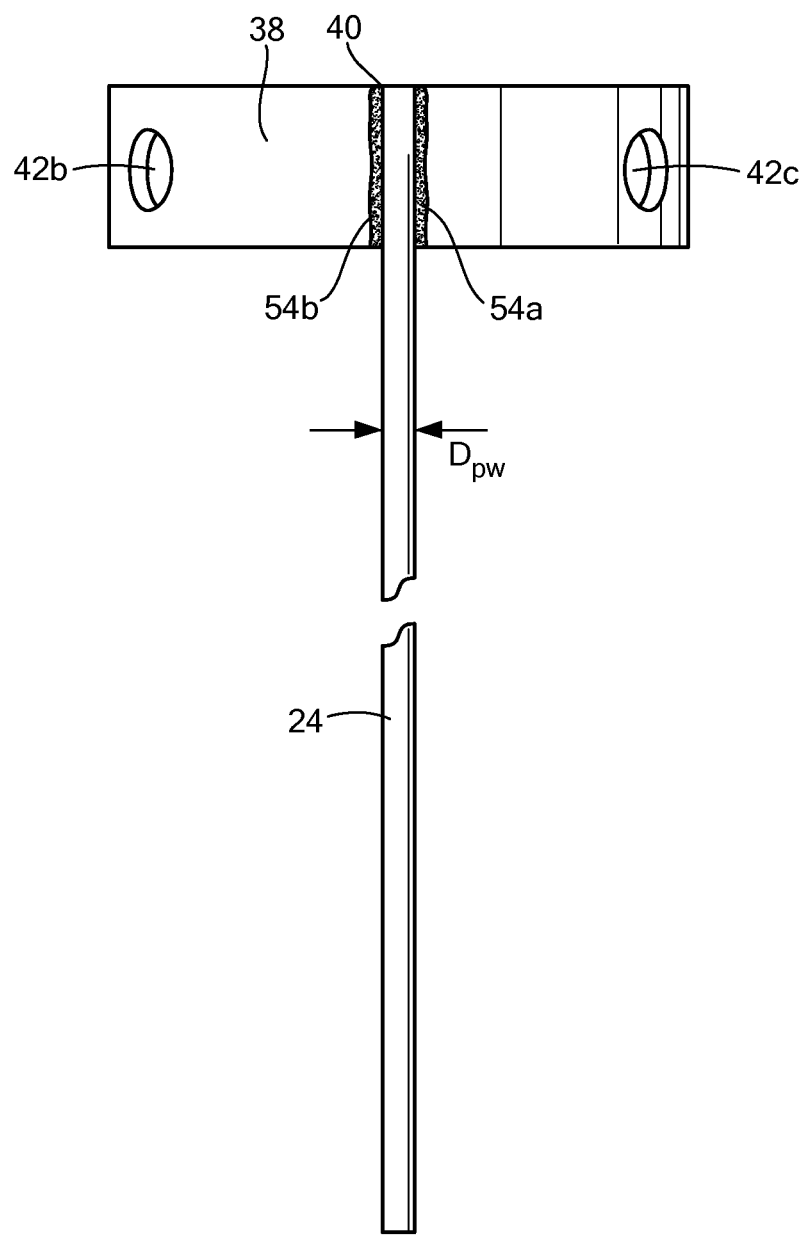
FIG. 9 shows a side view of a straight round pull wire received within and welded to the second embodiment of a pull wire anchor.
Figure 10:
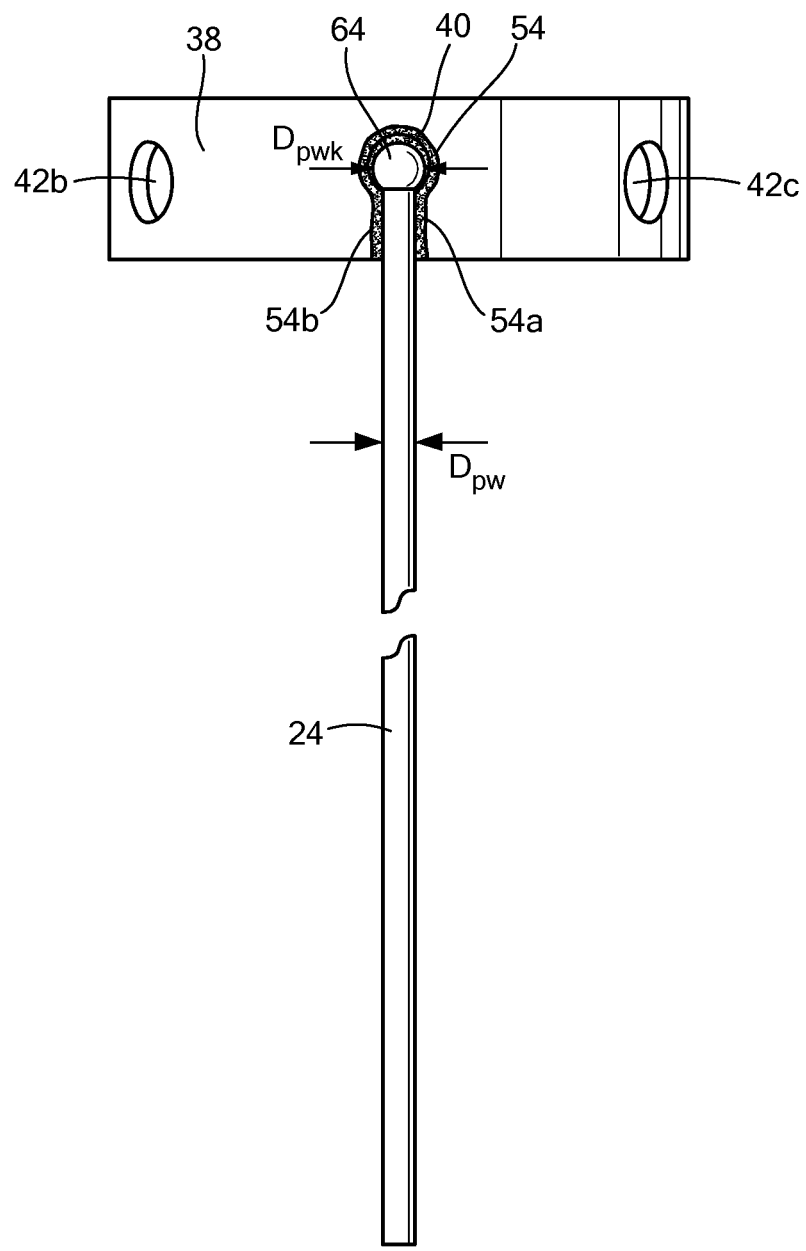
FIG. 10 shows a side view of a knobbed round pull wire received within and welded to the third embodiment of a pull wire anchor.

Continuing to refer to FIG. 5, the pull ring 38 may include a single receiving slot 40 if only one pull wire 24 is used for steering the distal end 18 of the catheter 14. In general, the receiving slot 40 may be substantially straight for receiving a straight rounded pull wire 24 (as shown in FIGS. 5 and 8), keyhole-shaped for receiving a knobbed round pull wire 24 (as shown in FIGS. 7 and 10), or may continue from the first edge to the second edge of the pull ring 38, thereby breaking the continuity of the entire pull ring 38 (as shown in FIGS. 2, 4, 6, and 9). The straight receiving slot 40 of FIG. 5 continues from the first edge 56 of the pull ring 38 to a distance $D_{RS}$ from the second edge 58, thereby preserving the continuity of only the second edge 58 and portion of the pull ring 38 proximate thereto. As a non-limiting example, the width $W_{RS}$ of the receiving slot 40 may be approximately 0.30 mm, and the height HRS may be approximately 1.14 mm. The distance $D_{RS}$ between the receiving slot 40 and the second edge 58 of the pull ring 38 may be, for example, between approximately 15% and approximately 55% of the height of the height H of the pull ring 38. However, the receiving slot 40 and pull ring 38 may have any measurements that are appropriate for the pull wire 24 and catheter 14 assembly used.

Continuing to refer to FIG. 5, the pull ring 38 may include any number of apertures 42, but will preferably include three or more. The purpose of the apertures 42 is to allow melted Pebax or similar thermoplastic 44/48 to flow through, each aperture 42 thereby serving as an anchor point between the catheter sheath inner lining 48 and the pull ring 38 (as shown and described in FIGS. 2 and 3). Accordingly, the apertures 42 are distributed about the pull ring 38 in a pattern that will counteract destructive pull forces exerted on the pull wire 24. For example, as shown in FIG. 5, the pull ring 38 may have a first aperture 42a, a second aperture 42b, and a third aperture 42c, each aperture 42a, 42b, 42c located equidistant from the first 56 and second edge 58 of the pull ring 38. The first aperture 42a is located approximately 180° from the receiving slot 40, creating an anchor point that is opposite the location of the pull force. Further, the second 42b and third 42c aperture may each be located between approximately 115° and approximately 125° from the first aperture 42a (that is, approximately 120°±5°). All degree measurements herein are calculated from an imaginary center point of an aperture 42a, 42b, 42c to an imaginary center line of the receiving slot 40. The apertures 42a, 42b, 42c may all have approximately the same diameter or they may be of different sizes and shapes. This distribution may be used in any embodiment having one receiving slot 40 and three apertures 42. Further, if more than three apertures 42 are included, each aperture 42 is approximately equidistant from the aperture 42 on either side.

Figure 6:
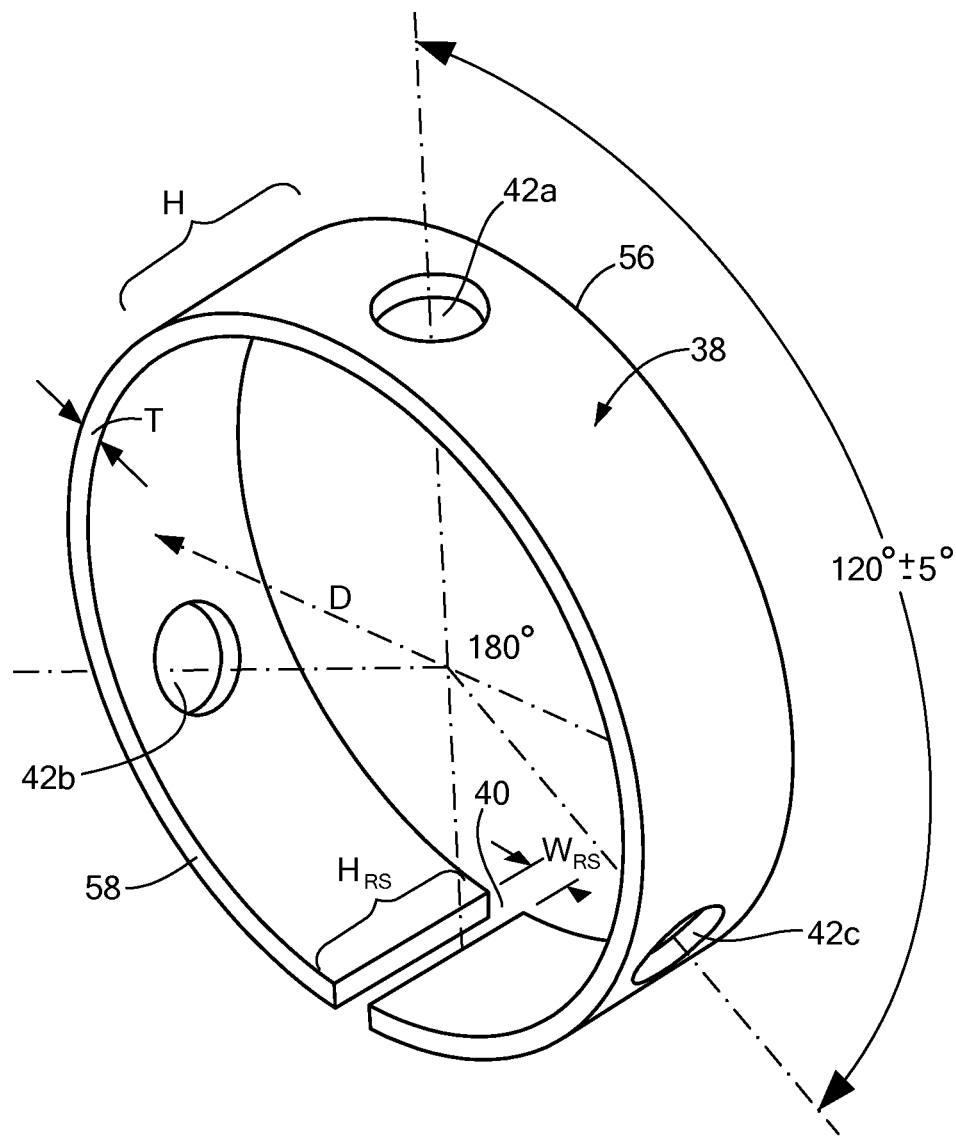
FIG. 6 shows a perspective view of a second embodiment of a pull wire anchor.

Referring now to FIG. 6, a second embodiment of a pull wire anchor 38 is shown. The pull ring 38 of FIG. 5 is similar to the pull ring 38 of FIG. 6, except for the receiving slot 40. The break-type receiving slot 40 of FIG. 6 extends from the first edge 56 all the way through the pull ring 38 to the second edge 58, thereby disrupting the continuity of the entire pull ring 38. Therefore the height $H_{RS}$ of the receiving slot 40 will be equal to the height H of the pull ring 38. The width $W_{RS}$ of the break-type receiving slot 40 may be similar to that of the straight receiving slot 40 of FIG. 5, and the break-type receiving slot 40 is sized to receive a straight round pull wire 24 (as shown in FIG. 9).

Referring now to FIG. 7, a third embodiment of a pull wire anchor 38 is shown. All measurements, materials, and other features of the pull ring 38 of FIG. 7 are the same as those of the pull ring 38 in FIGS. 1-6, except for the receiving slot 40 and number and distribution of apertures 42. The pull ring 38 of FIG. 7 includes a first 40a and second 40b receiving slot having a keyhole shape, with a substantially straight lower portion 60 abutting the first edge 56 and having a width $W_{L-RS}$, and a rounded upper portion 62 closer to the second edge 58 having a width $W_{U-RS}$. The keyhole-type receiving slots 40a, 40b are approximately 180° from each other and are sized to receive a knobbed round pull wire 24 (as shown in FIG. 10). The keyhole-type receiving slot 40a, 40b of FIG. 7 continues from the first edge 56 of the pull ring 38 to a distance DRS from the second edge 58, thereby preserving only the continuity of the second edge 58 and a portion of the pull ring 38 proximate thereto (as in FIG. 5). The pull ring 38 further includes a first aperture 42a, second aperture 42b, third aperture 42c, and fourth aperture 42d. The first 42a and third 42c apertures are located approximately 180° from each other, and the second 42b and fourth 42d apertures are located approximately 180° from each other. Further, the first 42a and second 42b apertures are each located between approximately 40° and approximately 50° (that is, approximately 45°±5°) from the first receiving slot 40a, and the third 42c and fourth 42d apertures are each located between approximately 35° and approximately 50° (that is, approximately 45°±5°)

from the second receiving slot 40*b*. This distribution may be used in any embodiment including four apertures 42 and two receiving slots 40.

Referring now to FIG. 8, a side view of a straight round pull wire 24 received within and welded to the first embodiment of a pull wire anchor 38 is shown. The pull ring 38 is as shown and described in FIG. 5, and the pull wire 24 has a circular cross section. The diameter $D_{PW}$ of the straight round pull wire 24 may be, as a non-limiting example, just under approximately 0.30 mm (for example, approximately 0.25 mm to approximately 0.29 mm) in order to fit within the receiving slot 40. Further, the diameter $D_{PW}$ of the pull wire 24 should be greater than the thickness T of the pull ring 38 (as shown in FIG. 4). The pull wire 24 is longitudinally received within the receiving slot 40. As a non-limiting example, the diameter $D_{PW}$ of the round pull wire 24 may be approximately 0.28 mm and the thickness T of the pull ring 38 may be approximately 0.15 mm. However, the round pull wire 24 may have any industry-accepted diameter, as long as the pull wire 24 is sized to fit within the receiving slot 40 of the pull ring 38 used. The round pull wire 24 may be composed of any suitable material, such as stainless steel, titanium, Nitinol, or alloy.

Once the pull wire 24 is fit within the receiving slot 40, the pull wire 24 is welded to the pull ring 38 along the edges of the receiving slot 40. Further, because the pull wire 24 has a diameter $D_{PW}$ that is greater than the thickness T of the pull ring 38, the pull wire 24 may be welded to the pull ring 38 in four discrete locations: two weld lines 54*a*, 54*b* on the outer surface 52 of the pull ring 38 along the receiving slot 40, and two weld lines 54*c*, 54*d* on the inner surface 50 of the pull ring 38 along the receiving slot 40 (shown in greater detail in FIG. 4).

Referring now to FIG. 9, a side view of a straight round pull wire 24 received within and welded to the second embodiment of a pull wire anchor 38 is shown. The dimensions of the straight round pull wire 24 in relation to the pull ring 38 and receiving slot 40 of the anchor mechanism 12 of FIG. 9 are approximately the same as those of the anchor mechanism 12 of FIG. 8. The weld characteristics are also similar, with four weld sites 54*a*, 54*b*, 54*c*, 54*d* available for attaching the round pull wire 24 to the pull ring 38. However, as shown in FIG. 9, each weld line will extend from the first edge 56 to the second edge 58 of the pull ring 38, and not just a portion thereof, as shown in FIG. 8.

Referring now to FIG. 10, a side view of a knobbed round pull wire 24 received within and welded to the third embodiment of a pull wire anchor 38 is shown. As for the anchor mechanisms 12 shown and described in FIGS. 8 and 9, the dimensions of the knobbed round pull wire 24 are such that the knobbed round wire 24 will fit within the keyhole-type receiving slot 40 of the pull ring 38. As a non-limiting example, the round wire may have a diameter $D_{PW}$ of approximately 0.25 mm and the width $W_{L-RS}$ of the lower substantially straight portion 60 of the keyhole-type receiving slot 40 may be approximately 0.30 mm. The same relationship applies for the substantially spherical knob 64 at the distal end of the knobbed round pull wire 24 and the upper rounded portion 62 of the keyhole-type receiving slot 40. As a non-limiting example, the diameter $D_{PWK}$ of the pull wire knob 64 may be approximately 0.38 mm and the diameter of the upper rounded portion 62 of the keyhole $D_{U-RS}$ may be approximately 0.42 mm. Both the knob 64 and the round pull wire 24 may be composed of any suitable material, such as stainless steel, titanium, Nitinol, or an alloy. Further, the knob 64 and the wire 24 may be composed of the same or different materials.

The weld characteristics of the keyhole-type anchor mechanism 12 are also similar, with four weld sites 54*a*, 54*b*, 54*c*, 54*d* available for attaching the round pull wire 24 to the pull ring 38. However, as shown in FIG. 10, additional weld sites 54 may be included between the knob of the pull wire 24 and the pull ring 38. Thus, both the keyhole shape and increased welding sites may further enhance the strength of the anchor mechanism 12 against destructive pull force.

It will be appreciated by persons skilled in the art that the present invention is not limited to what has been particularly shown and described herein above. For example, any combination of number or type of receiving slots and apertures may be used. In addition, unless mention was made above to the contrary, it should be noted that all of the accompanying drawings are not to scale. A variety of modifications and variations are possible in light of the above teachings without departing from the scope and spirit of the invention, which is limited only by the following claims.

What is claimed is:

1. A catheter steering device, the device comprising:
a substantially annular band having an outer surface and an inner surface and defining a receiving slot that extends between the outer surface and the inner surface, the receiving slot being sized to longitudinally receive a portion of wire having a circular cross section, the wire coupled to the receiving slot in two or more locations,
the band including a first aperture, a second aperture, and a third aperture, each of the first, second, and third apertures extending between the inner surface and the outer surface of the band,
the band further including a thickness, a first edge, a second edge, and a height between the first edge and second edge, the height of the band being greater than the thickness of the band.

2. The device of claim 1, wherein the wire is welded to the band in four locations.

3. The device of claim 1, wherein a center point of the first aperture is located approximately 180° from a center line of the receiving slot.

4. The device of claim 3, wherein a center point of the second aperture and a center point of the third aperture are each located between approximately 120° from either side of the center point of the first aperture.

5. The device of claim 4, wherein each of the apertures is circular in shape.

6. The device of claim 5, wherein the band includes a first, a second, a third, and a fourth aperture, and a first and second receiving slot.

7. The device of claim 6, wherein a center point of the first aperture and a center point of the second aperture are each located between approximately 40° and approximately 50° from either side of a center line of the first receiving slot, and a center point of the third aperture and a center point of the fourth aperture are each located between approximately 40° and approximately 50° from either side of a center line of the second receiving slot, and wherein the center points of the first and second apertures are located approximately 180° from each other.

8. The device of claim 7, wherein each receiving slot has a keyhole shape.

9. The device of claim 4, wherein the apertures are each equidistant from the first edge and second edge, the receiving slot continuing from the first edge to a distance from the second edge.

10. The device of claim 9, wherein the distance from the second edge is between approximately 10% to approximately 50% of the entire height of the band.

11. The device of claim 9, wherein the receiving slot has a keyhole shape, the widest part of the keyhole shape being located between the first edge and the second edge of the band.

12. The device of claim 9, wherein the receiving slot continues from the first edge to the second edge.

13. A catheter steering assembly, the assembly including:
a catheter pull wire having a distal end, a proximal end, and a length therebetween, the distal end, the proximal end, and the length each having a circular cross section; and
a continuous annular band including an inner face and an outer face and defining at least one receiving slot extending between the inner face and the outer face, the at least one receiving slot being sized to receive the distal end of the catheter pull wire,
the continuous annular band further defining a first edge, a second edge, and a height therebetween, each aperture being equidistant from the first edge and second edge, and the at least one receiving slot continuing from the first edge to a distance from the second edge,
the continuous annular band further defining a first aperture, a second aperture, and a third aperture, each of the first, second, and third apertures, extending between the inner face and the outer face, a center point of the first aperture being located approximately 180° from the receiving slot, and a center point of the second aperture and a center point of the third aperture each being located approximately 120° from either side of the center point of the first aperture.

14. The assembly of claim 13, wherein:
the distal end of the pull wire has a substantially spherical knob on the distal tip; and
the receiving slot has a keyhole shape, the widest part of the keyhole shape being located between the first edge and the second edge of the band, the keyhole shape sized to receive the knobbed distal end of the pull wire.

15. A catheter steering assembly, the assembly including:
a catheter pull wire having a distal end, a proximal end, and a length therebetween, the distal end including a substantially spherical knob defining a maximum diameter, the proximal end and the length each having a circular cross section defining a diameter that is less than the maximum diameter of the substantially spherical knob; and
a continuous annular band defining a keyhole-shaped receiving slot, a widest part of the keyhole-shaped receiving slot being sized to receive the substantially spherical knob of the distal end of the catheter pull wire.

* * * * *